(12) United States Patent
Strittmatter

(10) Patent No.: US 6,348,322 B1
(45) Date of Patent: *Feb. 19, 2002

(54) METHOD OF SCREENING FOR SPECIFIC BINDING INTERACTIONS

(75) Inventor: Warren J. Strittmatter, Durham, NC (US)

(73) Assignee: Duke University, Durham, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/953,323

(22) Filed: Oct. 17, 1997

(51) Int. Cl.[7] .................. G01N 33/53; G01N 33/543; G01N 33/546; G01N 33/552
(52) U.S. Cl. ................. 435/7.8; 435/6; 435/7.1; 435/174; 435/287.2; 435/287.9; 435/968; 436/518; 436/523; 436/527; 436/528; 436/529; 436/534; 436/172; 436/805; 436/807; 530/811; 530/812; 422/55; 422/57; 422/82.05; 422/82.08
(58) Field of Search ..................... 435/6, 7.1, 7.8, 435/174, 180, 181, 287.2, 287.9, 288.7, 961, 962, 968, 973; 436/501, 518, 523, 524, 527, 528, 529, 531, 534, 172, 800, 805, 807; 530/811, 812; 422/50, 55, 57, 82.05, 82.08

(56) References Cited

U.S. PATENT DOCUMENTS

| | | | |
|---|---|---|---|
| 4,868,103 A | * | 9/1989 | Stavrianopoulos et al. ..... 435/6 |
| 5,143,854 A | | 9/1992 | Pirrung et al. ............... 436/518 |
| 5,194,393 A | * | 3/1993 | Hugl et al. .................. 436/527 |
| 5,405,783 A | | 4/1995 | Pirrung et al. ............... 436/518 |
| 5,510,270 A | | 4/1996 | Fodor et al. ................. 436/518 |
| 5,565,324 A | | 10/1996 | Still et al. ........................ 435/6 |
| 5,711,915 A | * | 1/1998 | Siegmund et al. ............. 435/6 |

OTHER PUBLICATIONS

Richard P. Haugland; *Handbook of Fluorescent Probes and Research Chemicals*, Sixth Edition:Page beginning "Fluorescence Resonance Energy Transfer" (1996).
Melamed et al.; An Historical Review of the Development of Flow Cytometers and Sorters, *Flow Cytometry and Sorting*, Second Edition:1–9 (1990).

* cited by examiner

Primary Examiner—Christopher L. Chin
Assistant Examiner—James L. Grun
(74) *Attorney, Agent, or Firm*—Myers Bigel Sibley & Sajovec, P.A.

(57) ABSTRACT

A method for detecting the binding of a test compound to a probe molecule comprises providing a test compound, the test compound having a first fluorophore bound thereto, and providing a screening substrate. The screening substrate comprises a solid support, a probe molecule bound to the solid support, and a second fluorophore bound to the solid support adjacent the probe molecule. An advantage of the invention is that this obviates the need for binding the second fluorophore directly to the probe molecule. Preferably, the second fluorophore is bound to the solid support by a flexible linker group. This enables the second fluorophore to interrogate different positions on the probe molecule, which is also bound to the solid support adjacent the linker group, enhancing the ability of the method of the invention to detect positive binding events (specific binding of the test compound to the probe molecule. The first and second fluorophores together comprise the donor and acceptor fluorophores of a fluorescence resonance energy transfer (FRET) pair, or a "donor/acceptor pair." The test compound is contacted to the screening substrate, and the screening substrate illuminated with light at a wavelength that is absorbed by the donor fluorophore. The transfer of energy from one to the other fluorophore is then detected, with the transfer of energy indicating the binding of the test compound to the probe. Substrates useful for carrying out the foregoing methods are also disclosed.

12 Claims, 3 Drawing Sheets

METHOD OF SCREENING FOR SPECIFIC BINDING INTERACTIONS

FIELD OF THE INVENTION

The present invention relates to methods and apparatus used to screen for specific binding interactions by fluorescent techniques. The methods are particularly useful for high throughput screening of such interactions in combinatorial libraries, including chip-based libraries, pin-based libraries, and split-pool libraries.

BACKGROUND OF THE INVENTION

The development of techniques for the screening of large numbers of different molecules for possible biological activity has become important in developing new drugs. Known as "combinatorial chemistry" techniques, these techniques typically involve the random generation of compounds to be screened. Combinatorial chemistry techniques are thus dramatically different from "rational drug" design techniques, where specific structures for new compounds are designed based on a knowledge of other active compounds or the target site of the compound. Instead, combinatorial chemistry relies on the large numbers of candidate compounds generated, and the rapid screening of those compounds, to provide a sufficient probability of identifying active compounds.

Numerous different combinatorial chemistry techniques are known. For example, U.S. Pat. No. 5,445,934 to Fodor et al. describes a substrate in which large numbers of different polymers, such as nucleotides or peptides, are affixed to discreet regions of that substrate for the screening thereof for biological activity. In another example, U.S. Pat. No. 5,565,324 to Still et al. reviews "split-pool" combinatorial libraries, and describes split pool libraries encoded with chemical tags.

The majority of work in developing new combinatorial chemistry techniques has focused on the methods for generating the combinatorial library, on the substrate structures for carrying the members of the library, or on the different structures from which the library can be comprised. Comparatively little attention has been devoted to developing new methods for detecting binding events within a combinatorial library. Accordingly, there is a need for new detecting methods that can be employed in conjunction with combinatorial chemistry techniques.

SUMMARY OF THE INVENTION

A method for detecting the binding of a test compound to a probe molecule comprises providing a test compound, the test compound having a first fluorophore bound thereto, and providing a screening substrate. The screening substrate comprises a solid support, a probe molecule bound to the solid support, and a second fluorophore bound to the solid support adjacent the probe molecule. An advantage of the invention is that this obviates the need for binding the second fluorophore directly to the probe molecule.

Preferably, the second fluorophore is bound to the solid support by means of a flexible linker group. This enables the second fluorophore to interrogate different positions on the probe molecule, which is also bound to the solid support adjacent the linker group. As discussed in greater detail below, this enhances the ability of the method of the invention to detect positive binding events (specific binding of the test compound to the probe molecule).

The first and second fluorophores together comprise the donor and acceptor fluorophores of a fluorescence resonance energy transfer (FRET) pair, or a "donor/acceptor pair." In preferred embodiments, the first and second fluorophores are different, the first and second fluorophores emit light at different wavelengths from one another, and the second fluorophore absorbs light at a wavelength emitted by the first fluorophore.

The test compound is contacted to the screening substrate, and the screening substrate illuminated with light at a wavelength that is absorbed by the donor fluorophore (which may be either the first or second fluorophore). The transfer of energy from one to the other fluorophore (that is, from the donor to acceptor fluorophore) is then detected (for example, by detecting the presence or absence of light emitted by the acceptor fluorophore) with the transfer of energy indicating the binding of the test compound to the probe.

The method is useful in diagnostic assays for the detection of a particular compound, or in high through-put, or combinatorial, screening of multiple compounds. The method can be employed as a competition assay, where the test compound competes for binding with a target compound, where the binding of the target compound indicates the absence of the test compound.

Since the acceptor fluorophore is excited only when the donor fluorophore is in close proximity thereto, an advantage of the present invention is that there need not be a step of separating the test compound from the solid support (for example, an intervening washing step) to distinguish non-specific binding from specific binding. For example, the entire process can be carried out in liquid, particularly aqueous, phase, by contacting a solution containing the test compound to the solid support, with the detecting step carried out while that solution is still in contact with the solid support.

The foregoing and other objects and aspects of the present invention are explained in detail below.

DETAILED DESCRIPTION OF THE INVENTION

Figure 1A:
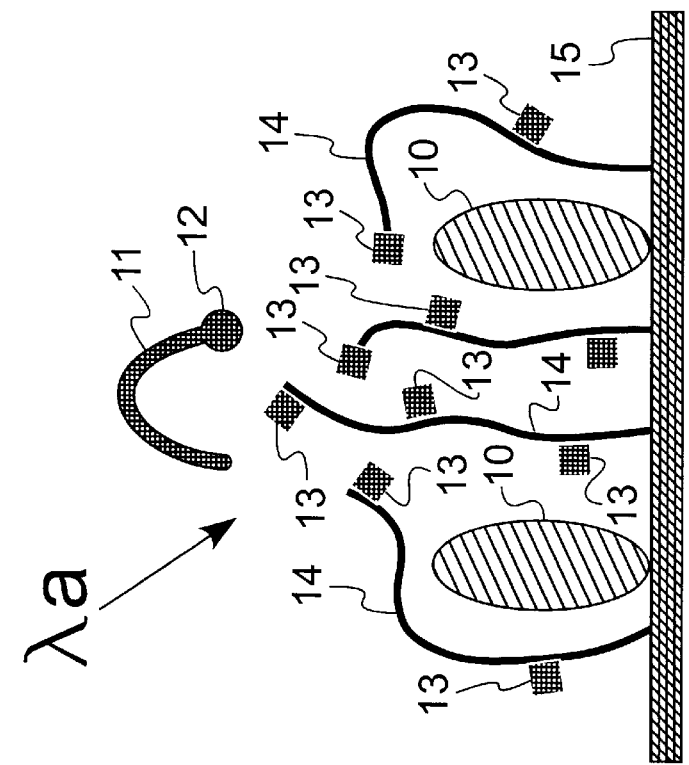
FIG. 1A schematically illustrates the method of the present invention, where the test compound binds to the probe compound and light is emitted at a second wavelength $\lambda_c$.
Figure 1B:
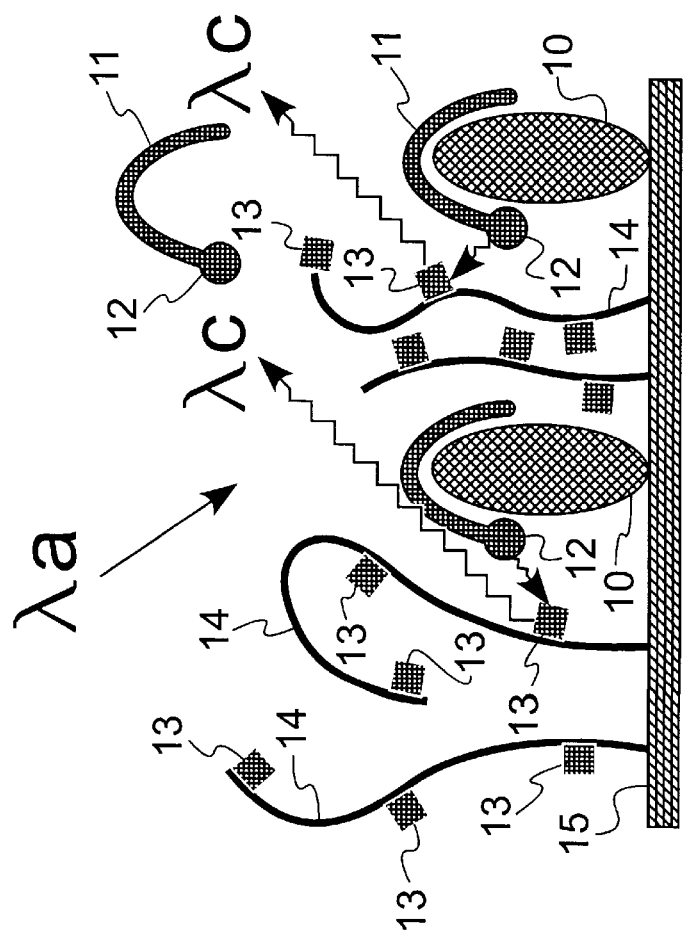
FIG. 1B schematically illustrates the method of the present invention, where the test compound does not bind to the probe compound.

Methods of the present invention are schematically illustrated in FIG. 1A and FIG. 1B. In overview, a test compound 11 has a first fluorophore 12 bound thereto, and a screening substrate comprising a solid support 15 has a plurality of probe molecules 10 bound thereto. A second fluorophore 13 is bound to a linker 14, which linker is in turn bound to the solid support. The screening substrate is illuminated with light at a wavelength $\lambda_a$ that is absorbed by the first fluorophore 12, which as illustrated is a donor fluorophore. The transfer of energy to the second fluorophore 13, here the acceptor fluorophore, is detected, here by detecting light at a second wavelength $\lambda_c$. As shown in FIG. 1A, light is emitted at the second wavelength $\lambda_c$. when the test compound 11, binds to the probe 10. As shown in FIG. 1B, light is not emitted at wavelength $\lambda_c$ when the test compound 11 is not bound to the probe 10.

Any suitable solid support can be used to carry out the present invention, and numerous different solid supports are well known to those skilled in the art. Examples of suitable materials from which the solid support may be formed include cellulose, pore-glass, silica gel, polystyrene, particularly polystyrene cross-linked with divinylbenzene, grafted copolymers such as polyethyleneglycol/polystyrene, polyacrylamide, latex, dimethylacrylamide, particularly cross-linked with N,N'bis-acrylolyl ethylene diamine and comprising N-t-butoxycarbonyl-N'acrylolyl hexamethylene diamine, composites such as glass coated with a hydrophobic polymer such as cross-linked polystyrene or a fluorinated ethylene polymer to which is grafted linear polystyrene, and the like. Thus the term "solid support" includes materials conventionally considered to be semi-solid supports. General reviews of useful solid supports that include a covalently-linked reactive functionality may be found in Atherton et al., *Prospectives in Peptide Chemistry*, Karger, 101–117 (1981); Amamath et al., *Chem. Rev.* 77:183 (1977); and Fridkin, The Peptides, Vol. 2, Chapter 3, Academic Press, Inc., pp 333–363 (1979). The solid support may take any suitable form, such as a bead or microparticle, a tube, a plate, a microtiter plate well, a glass microscope cover slip, etc.

The present invention can be used with probe molecules, or libraries (where groups of different probe molecules are employed), of any type. In general, such probe molecules are organic compounds, including but not limited to that may be used to carry out the present include oligomers, non-oligomers, or combinations thereof. Non-oligomers include a wide variety of organic molecules, such as heterocyclics, aromatics, alicyclics, aliphatics and combinations thereof, comprising steroids, antibiotics, enzyme inhibitors, ligands, hormones, drugs, alkaloids, opioids, benzodiazepenes, terpenes, prophyrins, toxins, catalysts, as well as combinations thereof. Oligomers include peptides (that is, oligopeptides) and proteins, oligonucleotides (the term oligonucleotide also referred to simply as "nucleotide, herein) such as DNA and RNA, oligosaccharides, polylipids, polyesters, polyamides, polyurethanes, polyureas, polyethers, poly (phosphorus derivatives) such as phosphates, phosphonates, phosphoramides, phosphonamides, phosphites, phosphinamides, etc., poly (sulfur derivatives) such as sulfones, sulfonates, sulfites, sulfonamides, sulfenamides, etc., where for the phosphorous and sulfur derivatives the indicated heteroatom for the most part will be bonded to C, H, N, O or S, and combinations thereof. Numerous methods of synthesizing or applying such probe molecules on solid supports (where the probe molecule may be either covalently or non-covalently bound to the solid support) are known, and such probe molecules can be made in accordance with procedures known to those skilled in the art. See, e.g., U.S. Pat. No. 5,565,324 to Still et al., U.S. Pat. No. 5,284,514 to Ellman et al., U.S. Pat. No. 5,445,934 to Fodor et al. (the disclosures of all United States patents cited herein are to be incorporated herein by reference in their entirety).

Test compounds used to carry out the present invention may be of any type, including both oligomers or non-oligomers of the types described above in connection with probe molecules above. Again, such test compounds are known and can be prepared in accordance with known techniques. Fluorophores can be bound to, or conjugated to, such test compounds in accordance with known techniques, preferably by covalently joining the fluorophore to the test compound. Such covalent joining includes the preparation of a fusion protein, such as a fusion protein of a test compound and a green fluorescent protein.

First and second fluoropohores that can be used to carry out the present invention can be selected based on the physical properties thereof, as is known in the art of fluorescence resonance energy transfer (FRET), the two being selected so that they together comprise the donor and acceptor fluorophores of an FRET pair. Either the first or the second fluorophore can serve as the donor fluorophore, with the other serving as the acceptor fluorophore.

FRET is a distance-dependent interaction between the electronic excited states of two fluorophores in which excitation is transferred from a donor molecule to an acceptor molecule without emission of a photon. In general, the primary conditions for FRET are (i) that the donor and acceptor molecules be in close proximity to one another (typically 1 or 10 to 100 or 200 Angstroms); (ii) that the absorption spectrum of the acceptor overlap the fluorescence emission spectrum of the donor; and (iii) that the donor and acceptor transition dipole orientations be approximately or essentially parallel. Examples of suitable donor and acceptor pairs include:

fluorescein and tetramethylrhodamine;

5-(2'-aminoethyl) aminonaphthalene-1-sulfonic acid (EDANS) and fluorescein;

EDANS and 4-(4'-dimethylaminopheylazo)benzoic acid (DABCYL);

fluorescein and fluorescein; and 4,4-difluoro-5-(2-thienyl)-4-bora-3a,4a diaza-5-indacene-3-propionic acid (BODIPY FL) and BODIPY FL.

See generally R. Haugland, Handbook of Fluorescent Probes and Research Chemicals (Sixth Ed. 1995). Abbreviations that are standard in the art are used herein. Note also that the present invention can be carried out when the donor and acceptor fluorophores are the same, with FRET being detected by the resulting fluorescence emission. *Biophys. J.* 69, 1565 (1995). As indicated above, one, or both, of the fluorophores can be a green fluorescent protein, and it is particularly advantageous to employ green fluorescent protein as the fluorophore when the test compound is a protein or peptide by preparing a fusion protein of the test compound and a green fluorescent protein.

Linking groups used to immobilize the fluorophore to the solid support carry out the present invention are, in general, polymers, including both water soluble polymers and water insoluble polymers (solubility referring to solubility when the linking group is free, rather than bound to the solid support). The polymers are elongate flexible chains of repeating monomeric units, and carry or contain functional groups along the chain length therof to which fluorophores can be conjugated. Numerous polymers that can be functionalized so that a fluorophore can be conjugated thereto, typically by a covalent bond, are known, and will be readily apparent to those skilled in the art. Examples include, but are not limited to, polysaccharides such as dextran, polyvinyl alcohol, polypeptides such as polylysine, and polyacrylic acid. The fluorophore may be bound to the linking group in any conformation or position, including to the free chain end thereof. However, in preferred embodiments of the invention, a plurality of fluorophores are conjugated to the polymer chain of the linking group at separate, spaced-apart locations along the length thereof. This enables excitation of the fluorophores even when the probe molecule binds to the target in different orientations, thereby enhancing the ability of the system to detect positive binding events.

Linking groups are covalently or non-covalently bound to the solid support in accordance with known techniques. For example, polymer linking groups can be covalently grafted onto a substrate polymer by any suitable reaction chemistry, such as free radical or condensation chemistry (e.g., polyacrylic acid linking groups may be covalently grafted onto a polypropylene substrate). In general, the same techniques used to prepare linking groups that are used to link probe molecules to solid supports for combinatorial chemistry can be used as the linking groups for the fluorophores herein. See, e.g., U.S. Pat. No. 5,624,711 to Sundberg et al. ("Derivatization of Solid Supports and Methods for Oligomer Synthesis)(the disclosure of which is incorporated by reference herein in its entirety).

Figure 2:
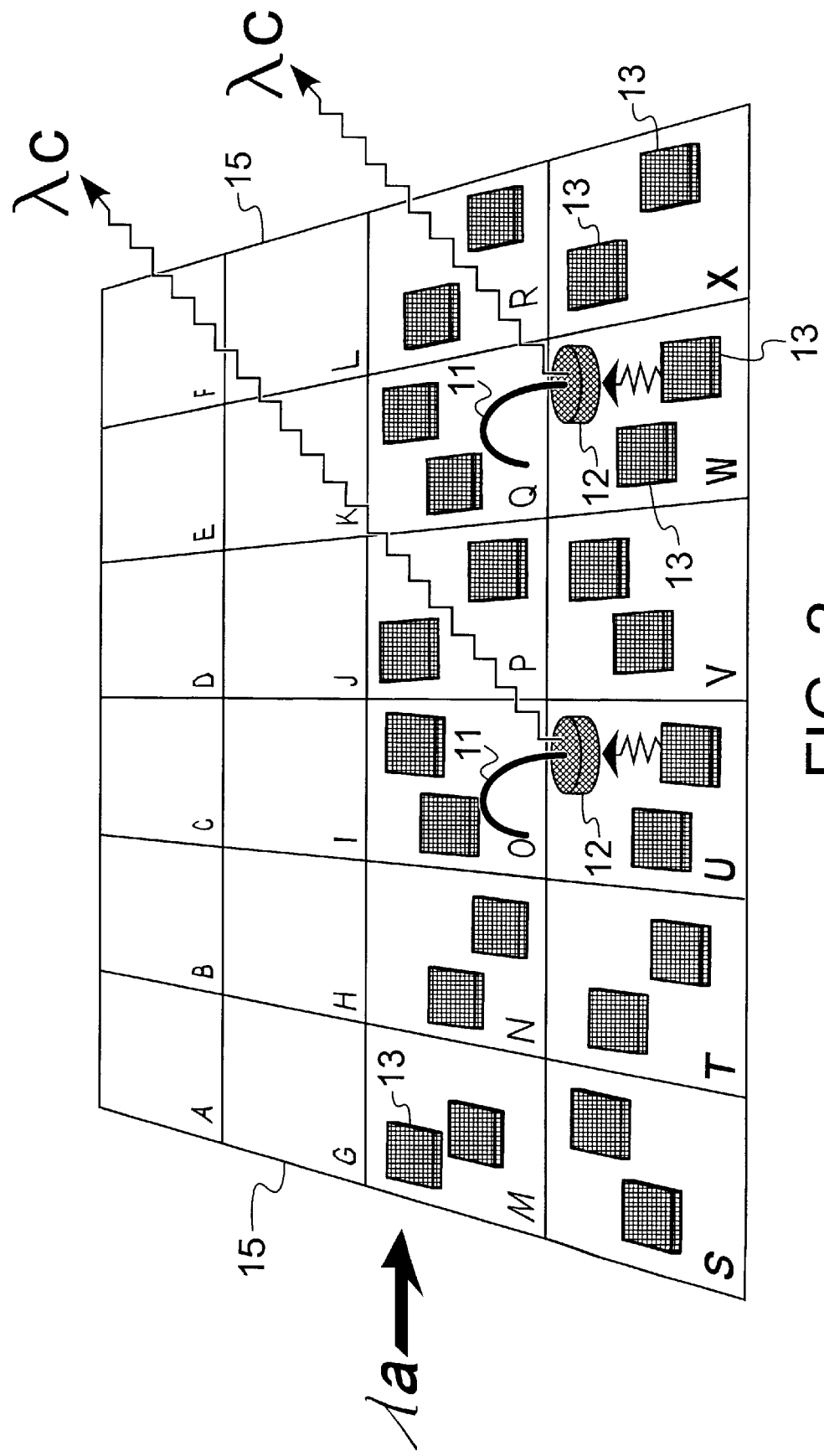
FIG. 2 illustrates a screening substrate carrying multiple different probes useful for carrying out the present invention.

The density of the linking groups on the solid support is such that one or more linking groups as described above, carrying one or more fluorophores, is positioned on the substrate a distance that will enable fluorescence resonance energy transfer between a first fluorophore on a test compound that binds to the probe and a second fluorophore on the linker bound to the solid support adjacent the probe. Where multiple different probes are on the substrate, each active probe will have such a spatial relationship with the linkers on the substrate. Typically, the density of the linking groups is sufficient so that the distance between one or more linking groups and the adjacent probe is not greater than 200 or 300 Angstroms from the probe molecule or molecules. The length, or average length, of the linking groups is not critical so long as it is sufficient to position fluorophores bound to the linking group effectively for FRET to or from fluorophores that are bound to test compounds that in turn bind to the probe molecules as described herein.

Where multiple different probe molecules are desired to be tested, a screening substrate useful for the high throughput screening of molecular interactions, such as in "chip-based" and "pin-based" combinatorial chemistry techniques, can be prepared in accordance with known techniques. As schematically illustrated in FIG. 2, the substrate comprises a solid support 15 having a surface portion, with the surface portion comprising a plurality of discreet known regions (A through X). A plurality of different probe molecules (not shown) are bound to the surface portion, with different probe molecules positioned on the surface portion in different ones of the discrete known regions. All can be prepared in accordance with known techniques. See, e.g., U.S. Pat. No. 5,445,934 to Fodor et al., U.S. Pat. No. 5,288,514 to Ellman, and U.S. Pat. No. 5,624,711 to Sundberg et al. In addition a plurality of the same fluorophores 13 are connected to or conjugated the surface portion, preferably by covalent bonding, with the fluorophores positioned on the surface portion in all of the plurality of discreet known regions (for clarity, fluorophores 13 are shown only in regions M through X). Connection of the fluorophores to the solid support is carried out in accordance with known techniques, or variations thereof that will be apparent to those skilled in the art, and can be carried out with linking groups as described above.

Methods for detecting the binding of a test compound to a probe molecule employing a screening substrate as described in connection with FIG. 2 above comprise, in general, providing a test compound 1, the test compound having a first fluorophore 12 bound thereto. A screening substrate as described above is provided, where the fluorophore bound to the surface portion of the solid support serves as a second fluorophore. The test compound is contacted to the screening substrate (typically by providing the test compound in a liquid, usually aqueous, solution), and the screening substrate illuminated with light at a wavelength that is absorbed by the first fluorophore. The presence or absence of light emitted by the second fluorophore in one of the discreet known regions is then detected, the emission of light from the second fluorophore indicating the binding of the test compound to the probe bound to that discreet known region.

Figure 3:
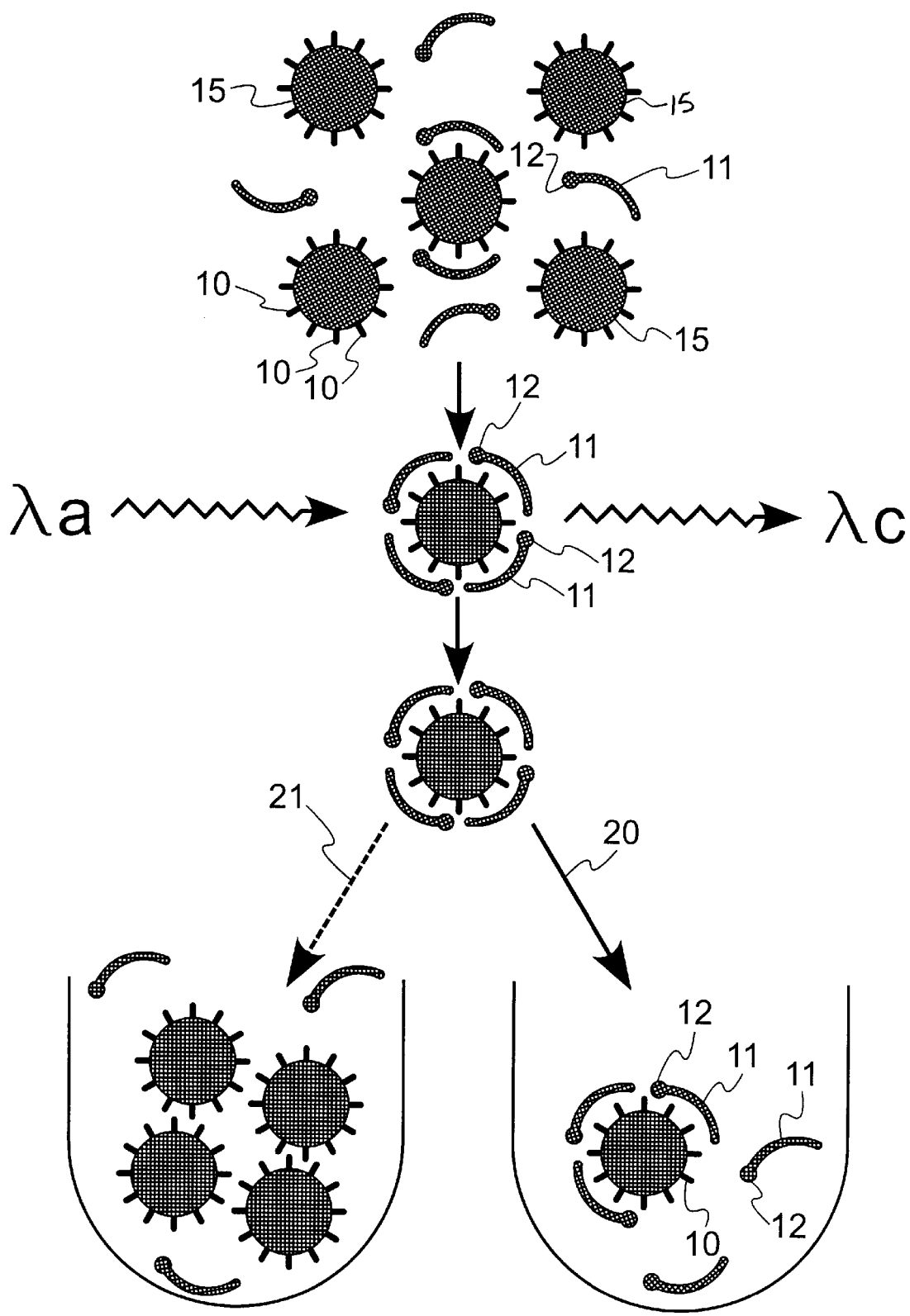
FIG. 3 illustrates a mixture of screening substrates, each carrying a different probe, useful for carrying out the method of the present invention.

In the alternative, screening of libraries of probe molecules may be carried out with mixtures of solid supports as used in "split-pool" combinatorial chemistry techniques. As schematically illustrated in FIG. 3, such mixtures comprise a plurality of discreet solid supports 15 each having a surface portion, each such support having a different probe molecule 10 bound to the surface portion thereof; and a plurality of the same fluorophores (not shown) bound to the surface portion of each of the solid supports (again, the second fluorophore is preferably bound the solid support by means of a linker group). Such mixtures can be prepared in accordance with procedures known in the art, and tag components can be added to the discreet solid supports in accordance with procedures known in the art. See, e.g., U.S. Pat. No. 5,565,324 to Still et al.

Methods of using mixtures of solid supports as shown in FIG. 3 above comprise providing a test compound, the test compound having a first fluorophore bound thereto, and providing a mixture of solid supports as described above. The test compound is then contacted to at least one of the discreet solid supports (typically by contacting the support to or immersing the support in a liquid, usually aqueous, solution containing the test compound), and the discreet solid support illuminated with light at a wavelength that is absorbed by the first fluorophore. The presence or absence of light emitted by the second fluorophore is then detected from the discreet solid support, the emission of light from the second fluorophore indicating the binding of the test compound to the probe bound to that discreet solid support.

An advantage of using mixtures of discreet solid supports in methods as described above is that the method can be carried out in solution or in a liquid phase, without the need for a step of separating unbound test compound from the solid support. Further, by passing the discreet solid supports continuously through a conduit, which conduit is associated with a fluorescent detector, while exciting the first fluorophore, and then separating those discreet solid supports where the second fluorophore emits light from those that do not (the separating step illustrated by arrows 20, 21), the method can advantageously be carried out in a fluorescent sorter in accordance with known techniques. See generally M. Melamed et al., An Historical Review of the Development of Flow Cytometers and Sorters, in Flow Cytometry and Sorting, pgs 1–9 (2d Ed. 1990). Such apparatus is generically referred to as flow sorting apparatus herein.

In various embodiments set forth above, the present invention has been explained with reference to the first fluorophore being the donor fluorophore, the first and second fluorophores being different, and the transfer of energy to the acceptor fluorophore being determined by the emission of light therefrom. While this is one preferred embodiment of the invention, it should be understood that either the first or the second fluorophore can be the donor, and that (where the donor and the acceptor are the same) the transfer of energy to the acceptor fluorophore can be still be detected by means such as detecting a characteristic fluorescence emission.

The present invention is explained in greater detail in the following non-limiting Examples, in which "M" means molar, "nm" means microliters.

EXAMPLE 1

Assay of Protein:Protein Binding by Fluorescence Resonance Energy Transfer

The purpose of this assay is to determine the domain of laminin recognized by a monoclonal anti-laminin antibody.

First, prepare synthetic peptides of 10 amino acids each which span the primary sequence of laminin. Then, each peptide is deposited into individual wells of a 96 well microtiter plate, along with fluorescein-bound dextran ($10^{-5}$M). After incubation for one hour remove the unbound peptide and the unbound dextran. Next, conjugate the anti-laminin antibody with tetramethylrhodamine, add $10^{-5}$M of the bound antibody to each well, and incubate the plate at room temperature for two hours. In a spectrofluorometer, assay each well for antibody-peptide interaction by exciting at 495 nm (the excitation frequency for fluorescein) and measuring emission at 570 nm (the emission frequency for rhodamine).

EXAMPLE 2

Assay of Protein:Protein Binding with Human:Anti-Human IgG

In a 96 well microtiter plate place a Bio-Rad cellulose paper insert into each well. Add 5μl of $10^{-6}$ M rhodamine-bound dextran, and 1μl of either rat or human IgG (equal to 32 picomoles) to each well.

Wash each well once with 100 μL of buffer, and then add 5 μL FITC-bound anti-human IgG, incubate at room temperature, and aspirate the media.

Fluorescence is then measured in a Perkin-Elmer LS50 spectrofluorometer, with an excitation frequency of 495 nm (the excitation frequency of FITC) and an emission frequency of 570 nm (the emission frequency of rhodamine). Results in fluorescence units for three different runs on two separate days are given in Table 1 below.

TABLE 1

| In well: | Rat IgG | Human IgG |
|---|---|---|
| Day 1: | 783 | 1000 |
|  | 897 | 973 |
|  | 817 | 979 |
| Day 2: | 490 | 521 |
|  | 525 | 572 |
|  | 457 | 538 |

Note the consistently higher levels of emissions for human IgG as compared to rat IgG in all runs.

The foregoing is illustrative of the present invention, and is not to be construed as limiting thereof. The invention is defined by the following claims, with equivalents of the claims to be included therein.

That which is claimed is:

1. A mixture useful for high throughput screening of molecular interactions, said mixture comprising:

a plurality of different solid support populations, each population comprising at least one discrete solid support, each said discrete solid support having a surface portion and having probe molecules and flexible linking polymers bound to the surface portion thereof;

the probe molecules bound to each said discrete solid support of one population being different from the probe molecules bound to each said discrete solid support of another population;

each of said flexible linking polymers having opposite end portions and a length dimension, each of said linking polymers being bound by one of said end portions to said solid support surface portion adjacent at least one of said bound probe molecules and having bound along said length thereof a plurality of fluorophore molecules, wherein each of said fluorophore molecules is a first member of a fluorescence resonance energy transfer pair of donor and acceptor fluorophore molecules, the same first pair member fluorophore molecules being bound, via said bound flexible linking polymers, onto each said discrete solid support in the mixture.

2. The mixture according to claim 1, wherein said probe molecules are proteins or peptides.

3. The mixture according to claim 1, wherein said probe molecules are nucleic acids.

4. The mixture according to claim 1, wherein said polymers are selected from the group consisting of polysaccharides, polypeptides, and polyacrylic acid.

5. The mixture according to claim 1, wherein each said discrete solid support in the mixture further comprises an additional tag component bound to the surface portion thereof, said tag component providing a detectable indication of which of the different probe molecules is bound to the discrete solid support.

6. The mixture according to claim 1, wherein each said discrete solid support is a bead having a diameter of 10 to 2000 μm.

7. A method for detecting binding of a test compound to a probe molecule, said method comprising:

(a) providing the mixture of claim 1;

(b) providing a test compound having a second fluorophore bound thereto, wherein the second fluorophore completes the fluorescence resonance energy transfer pair of donor and acceptor fluorophore molecules with the first pair member fluorophore molecules bound onto the discrete solid supports in the mixture;

(c) contacting said test compound with the mixture under conditions suitable for binding of test compound to any probe molecules, bound onto the discrete solid supports therein, capable of binding the test compound;

(d) illuminating at least one of said contacted discrete solid supports in the mixture with light of a wavelength that is absorbed by said donor fluorophore molecule; and then (e) detecting transfer of fluorescence resonance energy to said acceptor fluorophore molecule from the illuminated at least one of said contacted discrete solid supports, the transfer indicating the binding of the test compound to the probe molecules bound to said illuminated at least one of said contacted discrete solid supports.

8. The method according to claim 7, wherein said polymers are selected from the group consisting of polysaccharides, polypeptides, and polyacrylic acid.

9. The method according to claim 7, wherein said contacting step is carried out by contacting a test solution containing said test compound with said mixture.

10. The method according to claim 9, wherein said illuminating step is carried out with said test solution remaining in contact with the discrete solid supports in the mixture.

11. The method according to claim 7, wherein said illuminating and detecting steps are sequentially repeated with sequential ones of said contacted discrete solid supports.

12. The method according to claim 11, wherein said illuminating and detecting steps are sequentially repeated in a flow sorting apparatus.

* * * * *

UNITED STATES PATENT AND TRADEMARK OFFICE
CERTIFICATE OF CORRECTION

PATENT NO. : 6,348,322 B1 Page 1 of 1
DATED : February 19, 2002
INVENTOR(S) : Strittmatter It is certified that error appears in the above-identified patent and that said Letters Patent is hereby corrected as shown below:

Column 2,
Line 42, should read as follows:
-- $\lambda_c$. --

Column 7,
Line 7, should read as follows:
-- rhodamine). --

Signed and Sealed this

Nineteenth Day of November, 2002

*Attest:*

JAMES E. ROGAN
*Attesting Officer*  *Director of the United States Patent and Trademark Office*